United States Patent [19]
Incavo et al.

[11] Patent Number: 5,964,763
[45] Date of Patent: Oct. 12, 1999

[54] INCREMENTALLY ADJUSTABLE TIBIAL OSTEOTOMY FIXATION DEVICE AND METHOD

[76] Inventors: Stephen J. Incavo, 55 Butler Dr., South Burlington, Vt. 05403; David L. Churchhill, 131 Main St., Apt. 601, Burlington; Bruce D. Beynnon, 91 Country Club Dr. East, South Burlington, both of Vt. 05401

[21] Appl. No.: 09/092,690

[22] Filed: Jun. 5, 1998

Related U.S. Application Data

[62] Division of application No. 08/801,055, Feb. 14, 1997, Pat. No. 5,827,286.

[51] Int. Cl.⁶ .................................................... A61B 17/80
[52] U.S. Cl. ................................................................ 606/71
[58] Field of Search ................................. 606/71, 70, 69, 606/87, 88, 89, 86, 82, 79

[56] References Cited

U.S. PATENT DOCUMENTS

| | | | |
|---|---|---|---|
| 3,604,414 | 9/1971 | Borges | 606/71 |
| 4,096,857 | 6/1978 | Cramer et al. | 606/71 |
| 5,129,903 | 7/1992 | Luhr et al. | 606/71 |
| 5,470,335 | 11/1995 | Du Tolt | 606/73 |
| 5,601,565 | 2/1997 | Huebner | 606/87 |
| 5,700,263 | 12/1997 | Schendel | 606/57 |
| 5,722,978 | 3/1998 | Jenkins, Jr. | 606/87 |
| 5,749,875 | 5/1998 | Puddu | 606/87 |

*Primary Examiner*—Michael Buiz
*Assistant Examiner*—David O. Reip
*Attorney, Agent, or Firm*—Domingue & Waddell, PLC

[57] ABSTRACT

A fully implantable, incrementally adjustable osteotomy fixation apparatus is disclosed. The apparatus comprises a first plate member, and a second plate member being telescopically received within the first plate member. The osteotomy fixation apparatus may further comprise a ratchet assembly, operatively associated with the first and second plate member, which allows for advancement of the first plate member relative to the second plate member, but prevents retraction. Attachment means operatively associated with the first and second plate members are provided for attaching the apparatus to the bone. The apparatus may also include an external extension brace, operatively associated with the ratchet, for extending the second plate member relative to the first plate member so that post-operative angular correction of the bone may be achieved. A method of performing an osteotomy to the bone is also disclosed utilizing the fixation apparatus herein disclosed.

6 Claims, 5 Drawing Sheets

INCREMENTALLY ADJUSTABLE TIBIAL OSTEOTOMY FIXATION DEVICE AND METHOD

This application is a divisional of application Ser. No. 08/801,055, filed Feb. 14, 1997, now U.S. Pat. No. 5,827, 286.

BACKGROUND OF THE INVENTION

This invention relates to an apparatus and method for performing an osteotomy. More particularly, but not by way of limitation, the invention relates to an apparatus and method for performing an osteotomy with an incrementally adjustable osteotomy fixation device. In this application, we describe its application to the most commonly performed osteotomy of the proximal tibia; however, the invention herein disclosed would apply to other bone or joint deformities.

All joints of the body, including the knee, are vulnerable to physical injury such as dislocation, fracture and/or damage by diseases such as arthritis and osteoporosis. As will be appreciated by those of ordinary skill in the art, a knee osteotomy is a procedure in which a section of bone is removed from either the upper tibia or distal femur in order to change the loading conditions at the knee. The knee osteotomy is generally performed by removal of a wedge of the bone so as to realign the remaining segments. A knee osteotomy may also be performed by adding a wedge of bone.

The osteotomy technique can serve to restore the anatomic and mechanical axes of the extremity. This operation is usually performed adjacent to the end of a bone, such as in the proximal region of the tibia, without removing the articular (end) surface, as would be the case for preparation of the bone for implantation of a joint prosthesis, such as a total knee prothesis. The procedure must be performed with a high degree of accuracy so that the end surface of the bone is not damaged and is subsequently correctly realigned to the desired orientation with respect to the alignment of the anatomic and mechanical axes of the bone.

An important consideration is the angle correction necessary for the reorientation. Prior art techniques of reorientation include cutting a predetermined wedge from the bone so as to leave intact a segment joining both portions of the bone. The bone portions are then drawn together to close the wedge shaped gap so that the sides there of engage. The bone portions may be secured and are allowed to heal in this new configuration.

In order to determine the angle correction, the geometry of the leg and the knee joint must be analyzed. Factors to consider for angular correction includes the forces affecting the knee joint (including but not limited to body weight, center of gravity, varus or valgus leg conditions, and the contact surface of the knee joint, etc). The magnitude and direction of forces acting upon the knee are a consequence of these and other factors. In the prior art, once these factors are considered, the angle and location of the osteotomy wedge may be chosen. Remember, the osteotomy changes the angle of the knee joint which in turn changes the distribution of forces along the contact surfaces of the joint.

The primary means of producing an angular correction to a joint include either a closing wedge or an opening wedge osteotomy. The closing wedge osteotomy does not work well because it decreases leg length and has a highly variable outcome. The prior art techniques used for a closing wedge osteotomy require that the surgeon create a wedge correction of a specific angle to make it conform to the bone during the initial osteotomy surgery. With this type of technique, all adjustments have to be made during the surgery. Once the wound is closed, no further changes can be made. This necessitates that all angular correction to the bone must be made during the initial surgery. The fixation device thus implanted will simply maintain that position until the bone heals. The opening wedge osteotomy works well if it is used in conjunction with external fixation hardware such as the Wagner method to provide adjustment during healing: However, this approach currently requires external fixation hardware to provide adjustments and this carries with its use the risk of infection. Further, external fixation is bulky and complicates the functional after care of a patient. Prior art devices for providing adjustment of an osteotomy during healing is the apparatus described by Robinson (U.S. Pat. No. 5,354,396). This device provides adjustment of the osteotomy site through an apparatus that extends through a patient's skin and therefore carries with its use the risk of infection and complications with regard to patient care. In addition, this device is designed for use on portions of the body that do not support body weight. Therefore, it would not be an effective approach to provide adjustment of an osteotomy about the knee. Another prior art device to provide adjustment of an osteotomy during healing is the apparatus described by Hildebrandt (U.S. Pat. No. 3,976, 060). This device is fully implantable and has a self powered system to provide adjustment of the osteotomy site. Its purpose is to extend a bone and by virtue of its size it could not be used to provide angular adjustment of an osteotomy.

Thus, there is a need for an apparatus and method for performing a tibial osteotomy that will allow for greater accuracy for determining the correct angle of orientation. There is also a need for a procedure and device that provides for incremental adjustment of the angular correction through the healing process. There is also a need for a fully implantable device which can be adjusted using an external force (or brace). There is also a need for an apparatus that will allow for incremental adjustment following the surgery. Further, there is a need for incremental adjustability of the device that provides an opening wedge type of osteotomy with gradual distraction.

SUMMARY OF THE INVENTION

A fixation apparatus for an osteotomy is disclosed. The apparatus comprises a first plate member, a second plate member being telescopically received within the first plate member, and a ratchet means, operatively associated with the first and second plate members, which will allow advancement of the first plate member relative to the second plate member in a first direction, but will prevent motion in the opposite direction. The apparatus additionally comprises attaching means for attaching the apparatus to the bone. In the preferred embodiment, the attaching means comprises two or more screw holes in the first plate member, and two or more screw holes in said second plate member through which bone screws are inserted to fix the apparatus to the bone.

In a further embodiment, the attaching means may comprise a blade formed on the end of the first and/or second plate members. Such a blade may be driven into the bone so as to achieve attachment of the plate to the bone. In yet a further embodiment, the attaching means may comprise a plurality of spikes fixed to the surface of the first and/or second plate members such that they be driven into the bone to facilitate attachment.

The osteotomy fixation apparatus may further comprise an override mechanism that, when actuated, will defeat the action of the rachet mechanism so as to freely allow motion in both directions of the first plate member relative to the second plate member.

In the preferred embodiment, in which the osteotomy fixation apparatus is especially adapted to the tibia, the second plate member comprises a first and second prong extending therefrom in a first and second plane, with the first prong adapted to partially encompass the tibia, and the second prong adapted to partially encompass the tibia. The first and second prongs will contain screw holes for attaching the second plate member to the tibia. Also in the preferred embodiment, the second plate member contains an angular deflection that is adapted to the curved contour of the tibia.

The osteotomy fixation apparatus may also include extension means, operatively associated with the ratchet means for extending the second plate member relative to the first plate member. In the preferred embodiment, in which the osteotomy fixation apparatus is especially adapted to the tibia, the extension means comprises a brace-like device applied externally to the skin in which a first pad is externally positioned to provide a first contact point with the medial femoral locality, a second pad is externally positioned to provide a second contact point with the medial tibial locality, and a third pad is externally positioned to provide a third contact point with the lateral tibial locality. In the preferred embodiment, the first pad is fixed relative to the first contact point, the second pad is fixed relative to the second contact point, and the third pad is incremental adjustable relative to the third contact point so that a lateral force may incremental be applied to the third contact point. This configuration will place the bone in three point bending such that the osteotomy site will tend to open on the side to which the osteotomy fixation apparatus is attached. Such opening will cause the first plate member to advance with respect to the second plate member.

A method of performing an osteotomy is also disclosed. The method comprises performing a transverse osteotomy to the bone, and thereafter, implanting a fixation device to the bone. Generally, the fixation device comprises a first plate member, a second plate member being telescopically received within the first plate member, and a ratchet means, operatively associated with the first and second plate members, which will allow advancement of the first plate member relative to the second plate member in a first direction, but will prevent motion in the opposite direction. The device additionally comprises attaching means for attaching the apparatus to the bone.

The method further comprises permitting the partial healing of the osteotomy of the bone before any angular change is introduced. Next, the limb is periodically placed within an extension brace. Thereafter, the angular orientation of the bone is measured while the limb is in the extension brace. A lateral force is applied to the third pad which in turn extends the second plate relative to the first plate so that the angular orientation of the bone is adjusted. Subsequent to removal of the extension brace, the rachet means maintains the angular adjustment by preventing retraction of the first plate member relative to the second plate member.

An advantage of the present invention includes having an apparatus that is fully implantable thereby avoiding the problem of infection through percutaneous pin tracts. Another advantage is that the only surgical procedures involved in using the apparatus are the procedures required to initially install the device and then to remove it at the completion of the treatment period. Yet another advantage is that the initial surgery is simplified since no angular correction needs to be achieved during surgery. Still yet another advantage includes the ability to incrementally adjust the angular correction during the treatment period. Typically, the treatment period lasts from 8 to 12 weeks.

Another advantage is that the invention herein disclosed allows for the continuous adjustment to the angular correction after the initial surgery is completed. This advantage means that the final angular correction does not need to be achieved during surgery, but can be gradually reached through periodic incremental adjustments. Continuous monitoring of the angular correction is possible during the treatment period so that the decision to arrest the correction can be made after having observed the effects of the correction.

Another advantage is that the load required to distract the bone segments in order to adjust the angulation is supplied by the externally applied brace. Yet another advantage is that the implantable device does not necessarily contain a motor, shape memory alloy, hydraulic cylinder or other load generating apparatus. Another advantage is that the device is simple and inexpensive to manufacture.

Yet another advantage of the present invention is that the incremental adjustability of the apparatus provides the opportunity to employ an opening wedge type of osteotomy with gradual distraction. Another advantage includes the preservation of the limb length. Still yet another advantage is that the device may be applied to any bone deformity.

A feature of the present invention includes a ratchet mechanism that allows for the incremental advancement of the telescopic plate members. Another feature includes attachment means by which the apparatus may be attached to the tibia. Still yet another feature includes use of an extension brace to generate a force so that the telescopic advancement of the device may be actuated.

DETAILED DESCRIPTION OF THE PREFERRED EMBODIMENTS

Figure 1A:
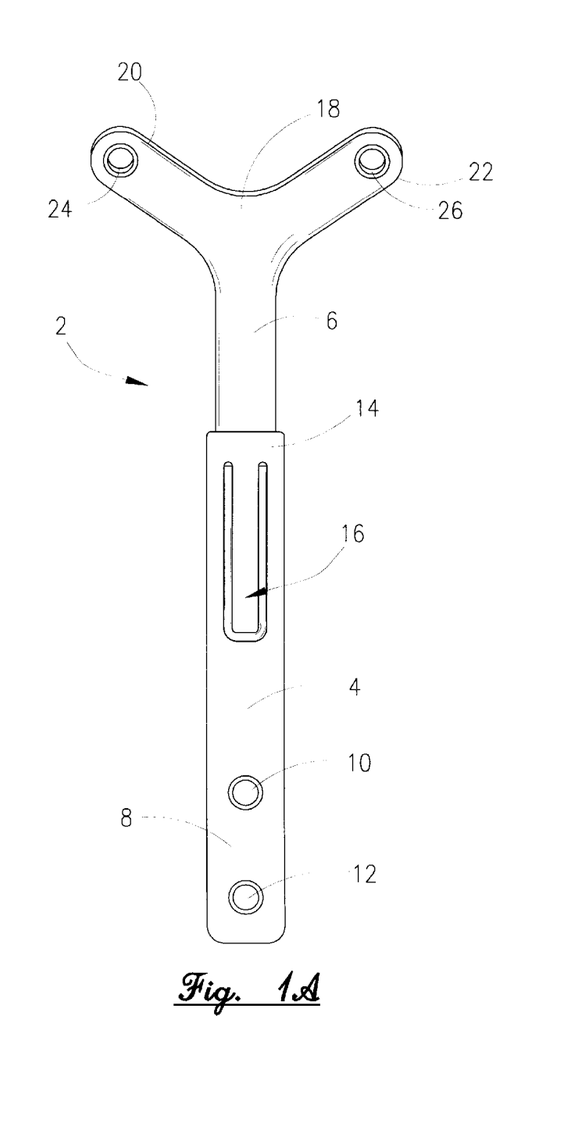
FIG. 1A is a front plan view of the fixation device of the present invention.

Referring now to FIG. 1A, the fixation device 2 of the present invention will now be described. Generally, the fixation device 2 contains a first plate member 4 that will have telescopically received therein a second plate member 6. The first plate member 4 will have a first end 8. The first end 8 may also be referred to as the distal end 8.

The first plate member 4 will also have a second end 14, with the second end having an opening that receives the second plate member 6. The second end 14 will have operatively adapted therewith a ratchet mean 16, operatively associated with the first plate member 4 and the second plate member 6, which will allow for advancment of the first plate member 4 relative to the second plate member 6. In one embodiment, the ratchet means 16 will be a pawl and groove/tooth 25 type of device that will allow advancement of the second plate member 6 in a first direction but will preclude direction in the opposite direction so that the second plate member 6 can only be advanced and not retracted. The ratchet member 16 may contain teeth located on the second plate member 6 with the pawl located on the first plate member 4. Other types of ratchet members 16 are possible such as a detent mechanism.

The first plate member 4 will also have attaching means 10,12 for attaching it to the bone. In one embodiment, the attaching means 10,12 will consist of screw holes 10,12 through which bone screws will attach the first plate member 4 to the bone. Other attaching means 10,12 are possible such as a blade, spikes or cerclage wires.

The second plate member 6 contains a first end (not shown) disposed within the first plate member 4 as well as a second end 18 representing the proximal end 18. In one embodiment, the proximal end 18 will have a first prong 20 and a second prong 22 extending therefrom.

The second plate member 6 will also have attaching means 24,26 for attaching it to the bone. In one embodiment, the attaching means 24,26 will consist of screw holes 24,26 through which bone screws will attach the second plate member 6 to the bone. Other attaching means 24,26 are possible such as a blade or spikes.

Figure 1B:
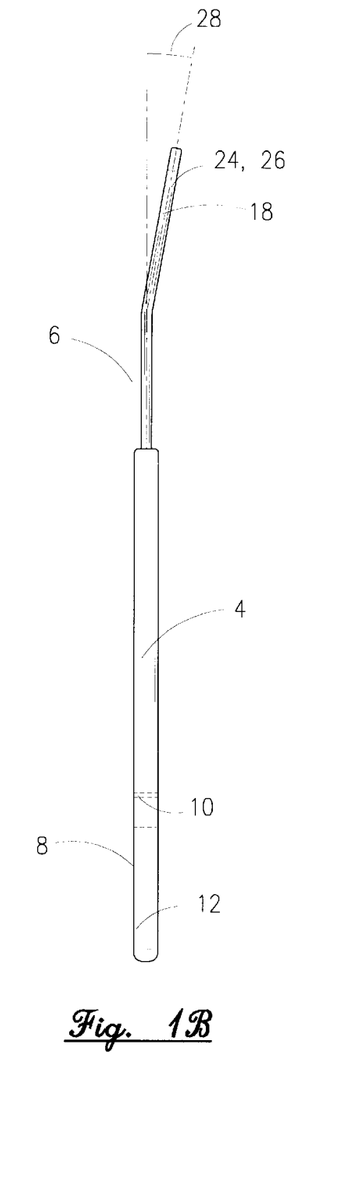
FIG. 1B is a side plan view of the device of FIG. 1A.

Referring now to FIG. 1B, a side plan view of the device 2 of FIG. 1A will now be described. Thus, the second plate member 6 contains a bend or curve, with the bend being an angle of deflection represented by the numeral 28. The angle of deflection 28 represents the general contour of the tibia. The angle of deflection may be varied depending on the particular contour of the patient's tibia. It should be noted that like numbers appearing throughout the various figures represent like components.

Figure 2A:
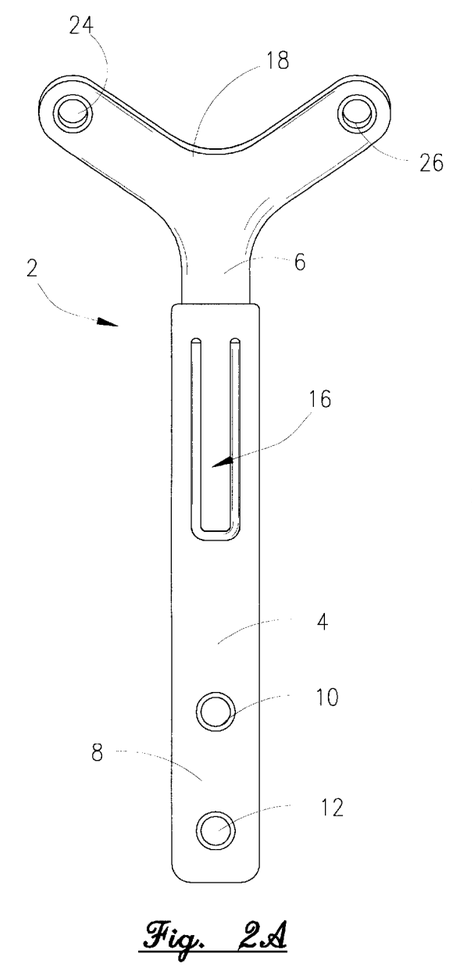
FIG. 2A is a front plan view of the fixation device depicted in a compressed configuration.
Figure 2B:
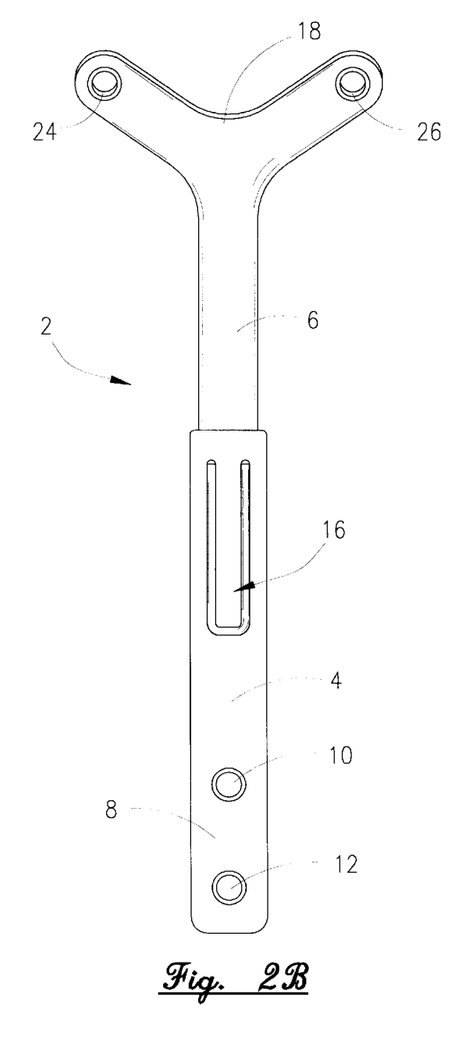
FIG. 2B is a front plan view of the fixation device of FIG. 2A depicted in an extended configuration.

In FIG. 2A, a front plan view of the fixation device 2 in a compressed position is shown. Thus, the compressed position of FIG. 2A depicts, for instance, the initial position the fixation device 2 is initially attached to the bone as will be more fully explained later in the description. In FIG. 2B, a front plan view of the fixation device 2 of FIG. 2A is depicted in an extended position. Therefore, in accordance with the teachings of the present invention, the second plate member 6 has been extended relative to the first plate member 4 and is maintained in that configuration by the ratchet means 16.

The extension of the second plate member 6 is initialized by the extension means (seen generally at in of FIGS. 5A and 5B) for extending the second plate member relative to the first plate member 4. The extension means is operatively associated with the ratchet member 16. The preferred embodiment of the extending means 30 will be described with the description of FIGS. 5A and 5B.

Figure 3A:
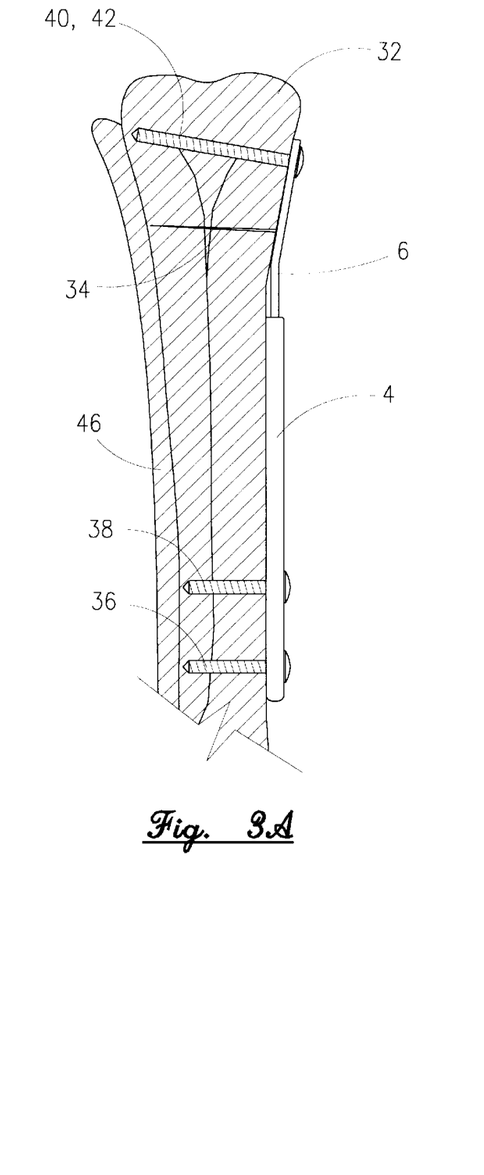
FIG. 3A is an illustrated view showing placement of the fixation device for medial opening wedge tibial osteotomy in the immediate post-operative configuration.
Figure 3B:
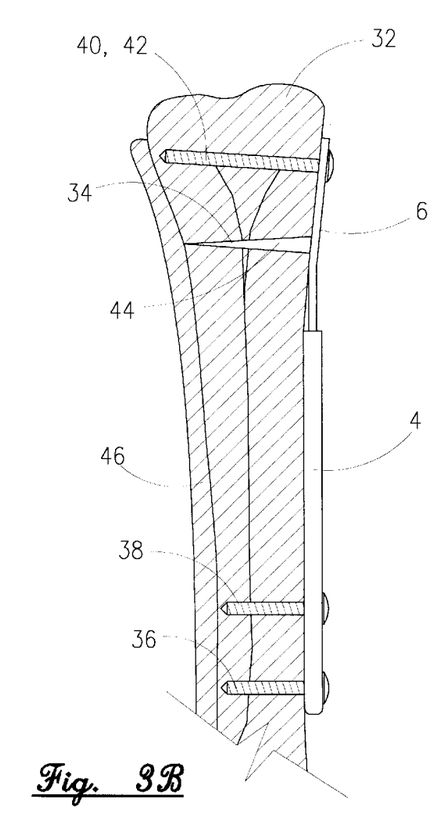
FIG. 3B is an illustrated view showing placement of the fixation device of FIG. 4A in the configuration at completion of the distraction period.
Figure 4:
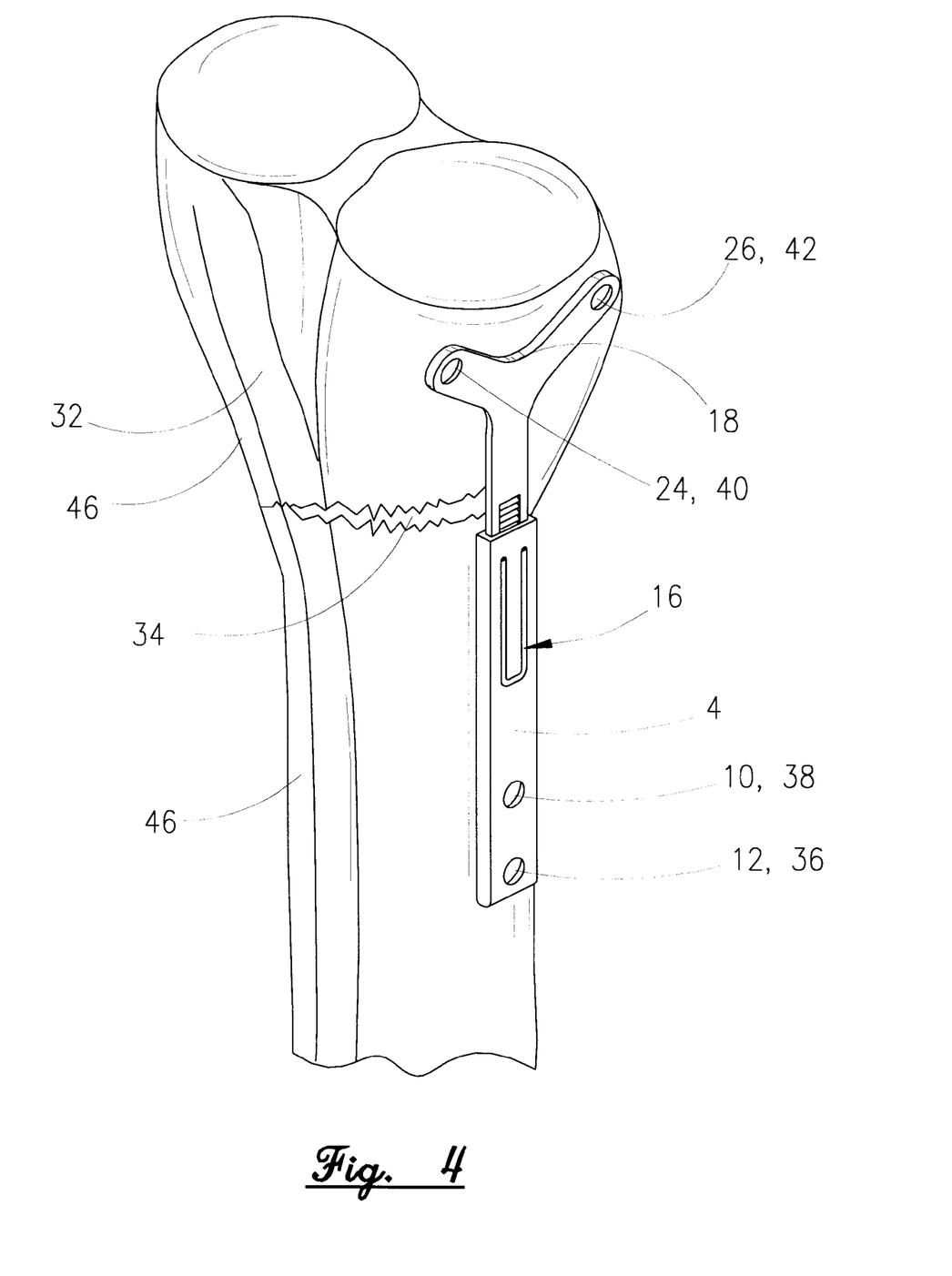
FIG. 4 is an illustrated view showing placement of the fixation device after the distraction period.

With reference to FIG. 3A, a view showing placement of the fixation device 2 for medial opening wedge osteotomy of the tibia in the post operative configuration is illustrated. Thus, the fixation device 2 is attached to the tibia 32. The surgeon has performed a transverse osteotomy or bone cut (seen generally at 34). The FIGS. 3A and 3B depict the screws 36, 38, 40, 42 inserted through the screw holes 10, 12, 24, 26, and therefore, implanted into the tibia 32. The FIG. 3A represents the immediate post-operative configuration while FIG. 3B represents the configuration at completion of the distraction period. More particularly, FIG. 3B represents the gap 44 that has occurred due to the distraction with the use of the extension means of FIGS. 5A and 5B. Also represented within FIGS. 3A and 3B is the fibula 46. FIG. 4 has also been presented in order to illustrate the fixation device 2 after the distraction period in relation to the medial, anterior, posterior and lateral views.

Figure 5A:
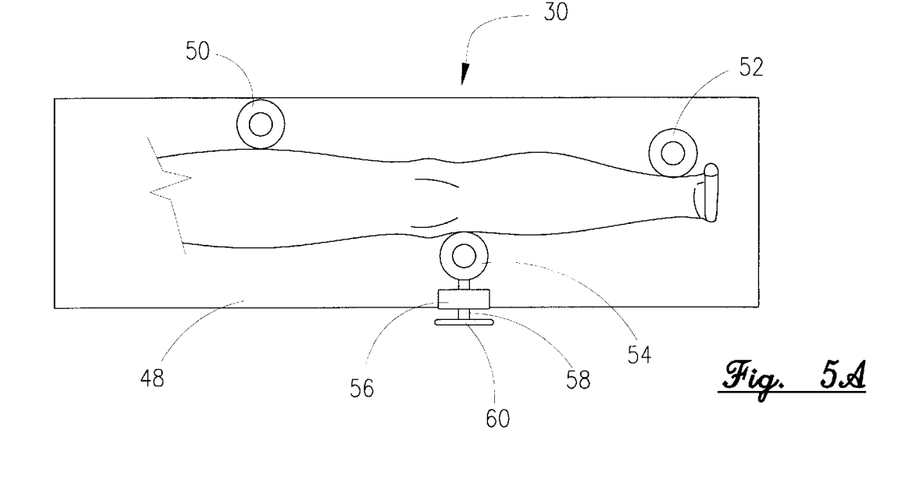
FIG. 5A is a top view showing placement of the extension brace being applied to the leg of the patient.

In FIG. 5A, an illustrated view showing placement of the extending means 30 being applied to the leg of the patient will now be described. In the preferred embodiment in which the osteotomy fixation apparatus is especially adapted to the tibia, the extension means 30 is an external extension brace 30 that will have a generally flat surface 48 so that the leg of the patient may be laid thereon as shown in FIG. 5A The external extension brace 30 contains a first pad 50 externally positioned to provide a first contact point with the medial femoral locality and a second pad 52 externally positioned to provide a second contact point with the medial tibial locality. In the preferred embodiment, the first pad 50 and second pad 52 will be fixed during the angular correction procedure.

Figure 5B:
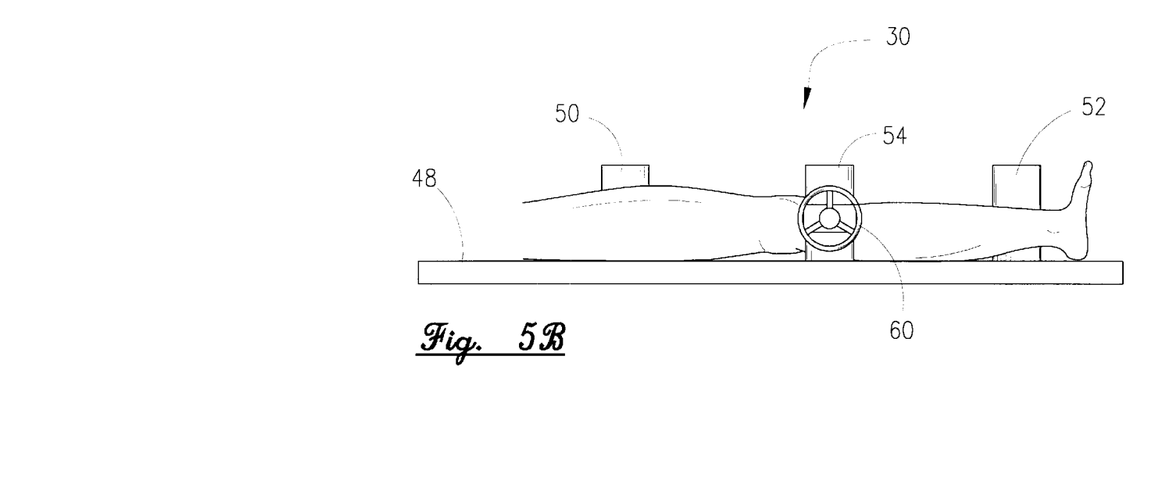
FIG. 5B is the side view of the extension brace depicted in FIG. 5A.

The external brace 30 will also include the third pad 54 externally positioned to provide a third contact point with the lateral tibial locality. The third pad 54 will be incremental adjustable relative to the third contact point so that a lateral force may be applied to the third contact point. In one embodiment, the third pad 54 contains a fixed plate 56 that will have an opening therein that has an internal thread profile. A lead screw 58 is contained therein, with the lead screw 58 having one end attached to the pad member 54 that provides the contact point and the other end having attached Ad thereto a handle member 60. Thus, the pad member 54 is advanced relative to the patients leg by the rotation of the handle 60 and lead screw 58 through opening of the fixed member 56.

Thus, the surgeon may turn the handle 60 and advance the lead screw 58 so that a three-point bending load is applied to the leg. The action of the advancement of the pad 54 coupled with the stationary pads 50, 52 will produce the force to be applied to the lateral tibial locality which will in turn cause the opening within the tibia to widen. Due to the novel design herein described, the plate member 6 is allowed to advance incrementally, but is prevented from retracting by the rachet means 16. Typically, small adjustments would be made periodically, for example one to seven degrees per week, until the desired total angular correction is reached. Of course any rate of adjustment could be used and is not limited by the fixation device 2. Other equivalent extension means 30 could be conceived of in which a four-point bending load is applied to the leg to effect the same result.

The method of performing a knee osteotomy using a fixation device 2 implanted to the tibia 32 in accordance with the teachings of the present invention will now be described. The method would include would performing a transverse or horizontal osteotomy incision (seen generally at 34 in FIG. 3A). Next, the fixation device 2 is implanted and attached to the bone via the attaching means 10,12,24,26. In the preferred embodiment, the attaching means consists of bone screws 38,36,40,42 inserted into the bone through the screw holes 10,12,24,25 respectively. The screws are rotated into the tibia as seen in FIGS. 3A and 3B, and thus, the fixation device 2 is attached to the tibia 32.

Next, the surgery is concluded and the wound closed. Thereafter, the wound and incision are allowed to heal for some period of time, with the period of time corresponding to a few days or up to two weeks.

Next, adjustments to the angular orientation may be made in accordance with the teachings of the present invention. Periodically, the patient is placed within the external extension brace 30 of FIGS. 5A and 5B. The surgeon will turn the handle 60 so that the lead screw 58 advances. The action of the advancement of the pad 54 coupled with the stationary pads 50, 52 will cause a lateral force to pad 54 which in turn widens the opening 34 within the tibia. Due to the novel design herein described, the second plate member 6 is allowed to advance incrementally relative to the first plate member 4 thereby allowing the opening 34 to widen. After removal of the extension brace 30, the rachet means 16 will prevent the opening 34 from subsequently narrowing. The surgeon would measure the incremental angular orientation of the tibia while the leg is in the external brace. Radiographic analysis would also confirm the incremental angular correction.

The angular correction to the tibia 32 may continue. Between each incremental angular adjustment, the opening 34 would be allowed to partially heal. Again, the gradual distraction procedure may be repeated as often as necessary in order to arrive at the optimum angular orientation. Once the gradual distraction procedure is concluded, the wedge gap 44 will be allowed to completely fill with natural bone growth. Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

We claim:

1. A method of performing an osteotomy comprising:

performing an initial transverse or horizontal osteotomy incision to the bone;

implanting a fixation device to the bone, with said fixation device comprising: a first plate having a first end and a second end; a second plate being telescopically received within said second end of said first plate member; attaching means for attaching said fixation device to the bone, a linear ratchet means, operatively associated with said first plate member and said second plate member, for allowing advancement of said first plate member relative to said second plate member, but preventing retraction of said first plate member relative to said second plate member;

permitting the partial healing of the incision to the bone;

placing a limb within an extension brace, said extension brace including: a first pad externally positioned to provide a first contact point; a second pad externally positioned to provide a second contact point; a third pad externally positioned to provide third contact point;

measuring the angular orientation oft he bone while the limb is in said external brace;

applying a lateral force to said third pad;

extending said second plate relative to said first plate so that the angular orientation of the bone is adjusted.

2. The method of claim 1 wherein the step of extending said second plate relative to said first plate comprises:

allowing advancement of said second plate relative to said first plate so that said second plate may be extended in a first direction;

preventing said second plate from being retracted relative to said first plate.

3. The method of claim 2 further comprising:

permitting the partial healing of the incision to the tibia;

measuring the angular orientation of the tibia relative to the femur while the leg is in said extension brace;

applying a force to said third pad;

extending said second plate member relative to said first plate to that the angular orientation of the tibia relative to the femur is adjusted.

4. A method of performing, an osteotomy comprising:

performing an initial transverse or horizontal osteotomy incision to the bone;

implanting a fixation device to the bone, with said fixation device comprising: a first plate having a first end and a second end; a second plate being telescopically received within said second end of said first plate member; attaching means for attaching said fixation device to the bone; a linear ratchet means, operatively associated with said first plate member and said second plate member, for allowing advancement of said first plate member relative to said second plate member, but preventing retraction of said second plate member;

placing a limb within an extension brace means for applying an external force to said linear ratchet means without penetrating the skin;

measuring the angular orientation of the bone while the limb is in said external brace;

applying an external force to the limb using said extension brace means;

extending said second plate relative to said first plate so that the angular orientation of the bone is adjusted.

5. The method of claim 4 wherein said ratchet means comprises a series of linear teeth formed on said first section of said second plate, said series of linear teeth interengaging and configured with a panel to allow for incremental movement:

engaging said linear teeth with said pawl;

allowing advancement of said second plate relative to said first plate so that said second plate may be extended in a first direction.

6. The method of claim 5 further comprising:

permitting the partial healing of the incision of the tibia;

measuring the angular orientation of the tibia relative to the femur while the leg is in said extension brace;

applying an external force to the limb using said extension brace means;

extending said second plate member relative to said first plate so that the angular orientation is adjusted.

\* \* \* \* \*

UNITED STATES PATENT AND TRADEMARK OFFICE
CERTIFICATE OF CORRECTION

PATENT NO. : 5,964,763
DATED : October 12, 1999
INVENTOR(S) : Incavo et al.

It is certified that error appears in the above-identified patent and that said Letters Patent is hereby corrected as shown below:

Title page,
Item [75] Inventors, change "Churchhill" to -- Churchill --.

Signed and Sealed this

Second Day of April, 2002

Attest:

JAMES E. ROGAN
Attesting Officer     Director of the United States Patent and Trademark Office